(12) United States Patent
White et al.

(10) Patent No.: US 11,400,254 B2
(45) Date of Patent: Aug. 2, 2022

(54) MICROCATHETER AND METHOD

(71) Applicant: Heraeus Medical Components LLC, St. Paul, MN (US)

(72) Inventors: Troy White, Maple Grove, MN (US); Joseph Kempf, Rosemount, MN (US); Dustin Andrist, Saint Paul, MN (US); Jacob Markham, Vadnais Heights, MN (US); Victoria K. Sandberg, Pine City, MN (US)

(73) Assignee: Heraeus Medical Components LLC, St. Paul, MN (US)

( * ) Notice: Subject to any disclaimer, the term of this patent is extended or adjusted under 35 U.S.C. 154(b) by 384 days.

(21) Appl. No.: 16/169,540

(22) Filed: Oct. 24, 2018

(65) Prior Publication Data

US 2019/0126005 A1  May 2, 2019

Related U.S. Application Data

(60) Provisional application No. 62/577,964, filed on Oct. 27, 2017.

(51) Int. Cl.
*A61M 25/00*  (2006.01)

(52) U.S. Cl.
CPC .... *A61M 25/0012* (2013.01); *A61M 25/0021* (2013.01); *A61M 25/0045* (2013.01); *A61M 25/0053* (2013.01); *A61M 2025/0042* (2013.01)

(58) Field of Classification Search
CPC .......... A61M 25/0012; A61M 25/0021; A61M 25/0045; A61M 25/0053; A61M 2025/0042
See application file for complete search history.

(56) References Cited

U.S. PATENT DOCUMENTS

| | | | | |
|---|---|---|---|---|
| 5,484,424 A | * | 1/1996 | Cottenceau | A61F 2/0105 604/525 |
| 5,554,139 A | * | 9/1996 | Okajima | A61M 25/005 600/433 |
| 5,569,220 A | * | 10/1996 | Webster, Jr. | A61M 25/0045 138/125 |
| 5,947,940 A | | 9/1999 | Beisel | |
| 5,951,539 A | * | 9/1999 | Nita | A61M 25/005 604/526 |

(Continued)

FOREIGN PATENT DOCUMENTS

| | | |
|---|---|---|
| EP | 0546094 | 6/1993 |
| EP | 1202769 | 5/2002 |

(Continued)

*Primary Examiner* — Dung T Ulsh
(74) *Attorney, Agent, or Firm* — Dicke, Billig & Czaja, PLLC (57) ABSTRACT

A microcatheter includes an inner polymeric tube defining an inner lumen. It includes a proximal section with an inner wire layer helically wound in a constricted state over the inner polymeric tube and includes an outer wire layer helically wound over the inner wire layer in a constricted state within the proximal section. It includes a distal section with a distal wire layer helically wound in a constricted state and having an outer diameter. The proximal and distal sections are joined. The outer diameter of the outer wire layer is substantially the same as the outer diameter of distal wire layer at the location where the proximal and distal sections are joined.

17 Claims, 8 Drawing Sheets

(56) References Cited

U.S. PATENT DOCUMENTS

| | | |
|---|---|---|
| 6,508,804 B2 | 1/2003 | Sarge et al. |
| 6,508,806 B1 | 1/2003 | Hoste |
| 6,685,696 B2 | 2/2004 | Fleischhacker et al. |
| 6,824,553 B1 | 11/2004 | Samson et al. |
| 7,621,904 B2 | 11/2009 | McFerran et al. |
| 7,896,861 B2 | 3/2011 | McFerran et al. |
| 7,905,877 B1 | 3/2011 | Jimenez et al. |
| 8,224,428 B2 | 7/2012 | Cui |
| 8,366,699 B2 | 2/2013 | Jimenez et al. |
| 8,403,912 B2 | 3/2013 | McFerran et al. |
| 8,702,680 B2 | 4/2014 | Jimenez et al. |
| 2001/0041881 A1* | 11/2001 | Sarge .............. A61M 25/005 604/525 |
| 2002/0156459 A1* | 10/2002 | Ye ................. A61L 29/085 604/527 |
| 2014/0207114 A1 | 7/2014 | Jimenez et al. |
| 2015/0250981 A1 | 9/2015 | Beasley et al. |
| 2015/0306347 A1* | 10/2015 | Yagi .............. A61M 25/0067 604/526 |
| 2016/0101262 A1 | 4/2016 | Root et al. |
| 2017/0072163 A1 | 3/2017 | Lim et al. |
| 2020/0129730 A1* | 4/2020 | Ishikawa .......... A61M 25/0012 |

FOREIGN PATENT DOCUMENTS

| | | |
|---|---|---|
| EP | 1804882 | 7/2007 |
| EP | 2133578 | 12/2009 |
| WO | 92/04072 | 3/1992 |
| WO | 2004/030015 | 4/2004 |

\* cited by examiner

MICROCATHETER AND METHOD

CROSS-REFERENCE TO RELATED APPLICATION

This Utility Patent Application claims priority to Provisional Patent Application No. 62/577,964, filed on Oct. 27, 2017, which is incorporated herein by reference.

BACKGROUND

One aspect relates to helically-wound microcatheter and related method. In many present microcatheter designs, in order to meet desired pushability and trackability requirements, the microcatheter may not have sufficient length to operate in some peripheral access applications. Where adequate length is provided, pushability and trackability requirements may not be met. Because of these and other limitations to previous approaches, there is a need for the present embodiments.

DETAILED DESCRIPTION

In the following Detailed Description, reference is made to the accompanying drawings, which form a part hereof, and in which is shown by way of illustration specific embodiments that may be practiced. In this regard, directional terminology, such as "top," "bottom," "front," "back," "leading," "trailing," etc., is used with reference to the orientation of the Figure(s) being described. Because components of the various embodiments can be positioned in a number of different orientations, the directional terminology is used for purposes of illustration and is in no way limiting. It is to be understood that other embodiments may be utilized and structural or logical changes may be made without departing from the scope of the embodiments. The following detailed description, therefore, is not to be taken in a limiting sense, and the scope of the embodiments is defined by the appended claims.

Figure 1:
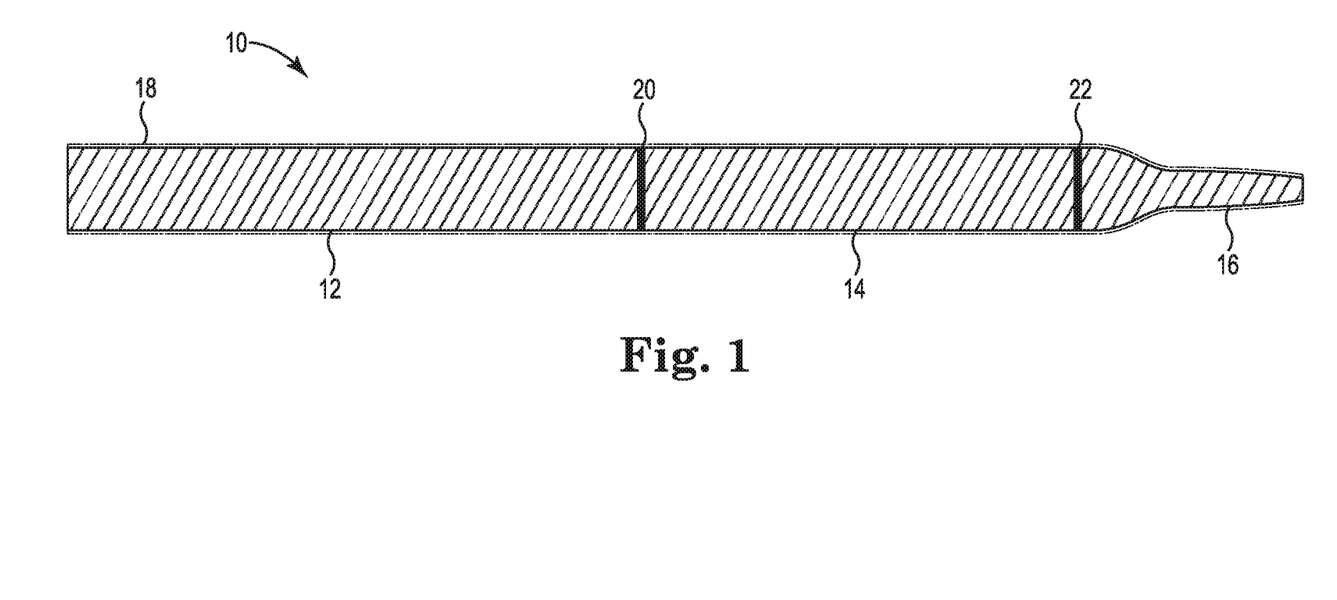
FIG. 1 illustrates a side view of a microcatheter in accordance with one embodiment.

FIG. 1 illustrates a microcatheter 10 in accordance with one embodiment. In one embodiment, microcatheter 10 includes a first proximal section 12, a second proximal section 14 and a distal section 16. In one embodiment, first proximal section 12 is coupled to second proximal section 14 at first junction 20 and second proximal section 14 is coupled to distal section 16 at second junction 22. All sections of microcatheter 10 are covered with a polymer cover 18. Although the wire layer and first and second junctions 20 and 22 below cover 18 are not actually visible through cover 18 when fully fabricated, cover 18 is ghosted for the illustration in FIG. 1 to show these features and relative locations.

In operation, microcatheter 10 is configured with a relatively small diameter and also with relatively thin walls, and is well suited to navigate the vast network of tiny arteries and veins found within the human or animal body. It can be used to deliver devices used in minimally invasive applications. Any number of proximal sections 12/14 can be used to establish a desired overall length for microcatheter 10. In one embodiment, as will be described in further detail below, proximal sections 12/14 are configured with multiple wire layers in order to provide excellent pushability, torqueability and trackability. In addition, in one embodiment, distal section 16 is coupled to one or more proximal sections 12/14, and is a single wire layer that provides excellent flexibility for navigating tortious vasculature. The overall lengths of each of the sections 12/14/16 illustrated in the Figures can be adjusted and are not meant to show relative proportions.

Figure 2:
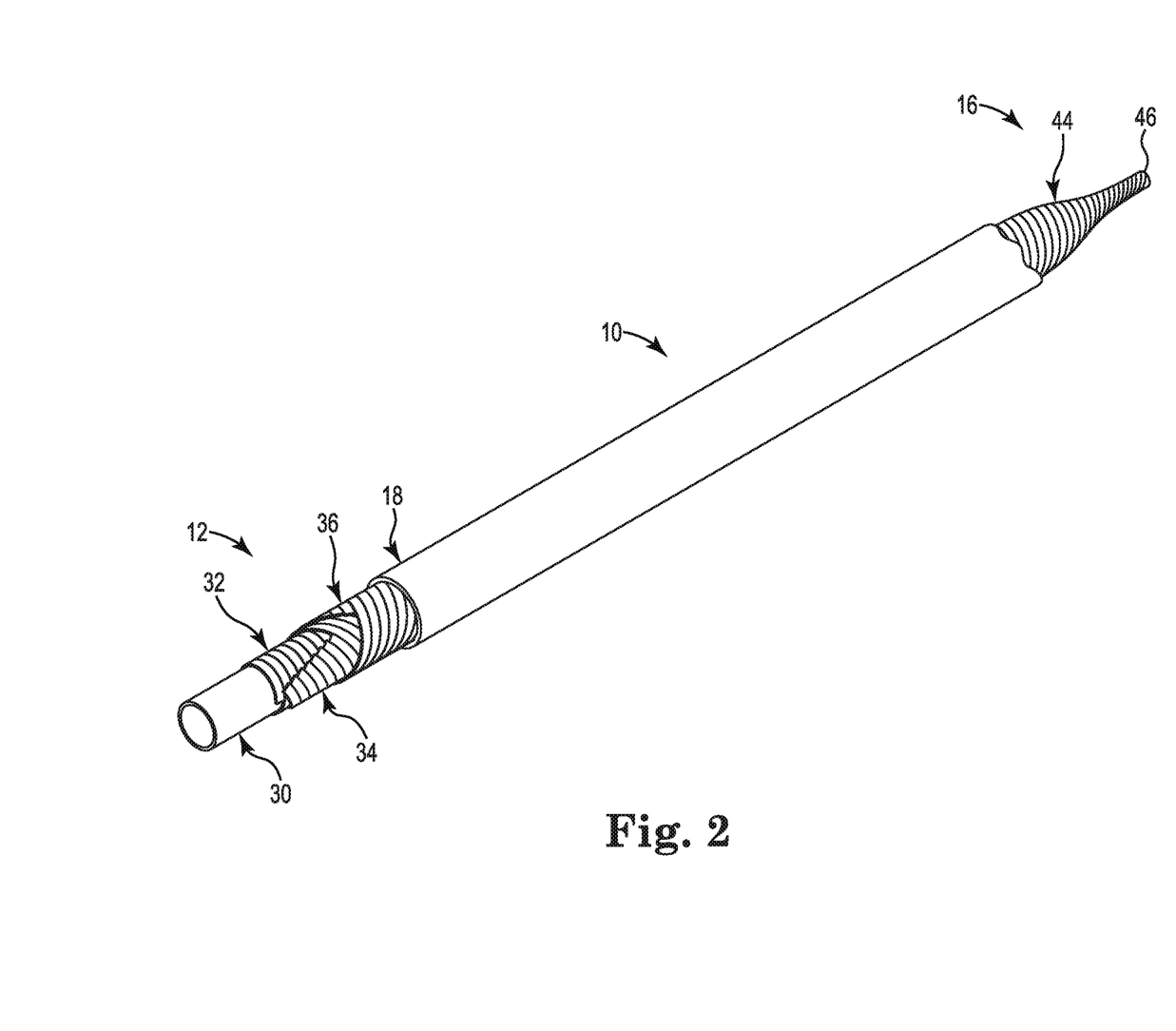
FIG. 2 illustrates perspective view, with cutaway portions, of a microcatheter in accordance with one embodiment.

FIG. 2 illustrates a partial cut-away perspective view of microcatheter 10 in accordance with one embodiment. In FIG. 2, portions of cover 18 are removed in first proximal section 12 and in distal section 16 to illustrate layers below.

In one embodiment, first proximal section 12 of microcatheter 10 includes a core 30, which in one embodiment is a tube-shaped layer of polymer material extending the length of microcatheter 10. In one embodiment, core 30 extends from the most proximal end of first proximal section 12, for example, at a hub, all the way out to a distal tip 46 of microcatheter 10. In other embodiments, core 30 can be shorter than the entire length of microcatheter 10, for example, not extending into distal section 16.

In one embodiment, first proximal section 12 of microcatheter 10 includes an inner wire layer 32 helically wound over core 30 (in FIG. 2, a portion of inner wire layer 32 is cut away to show core 30 below it). An intermediate wire layer 34 is helically wound over inner wire layer 32 (in FIG. 2, a portion of intermediate wire layer 34 is cut away to show inner wire layer 32 below it). In one embodiment, microcatheter 10 further includes an outer wire layer 36 helically wound over intermediate wire layer 34 (in FIG. 2, a portion of outer wire layer 36 is cut away to show intermediate wire layer 34 below it). Outer polymer cover 18 is formed over the combination of core 30, inner wire layer 32, intermediate wire layer 34, and outer wire layer 36, thereby securing the combination together.

In one embodiment, microcatheter 10 also includes second proximal section 14 coupled between first proximal section 12 and distal section 16. In one embodiment, second proximal section 16 also has three wire layers, similar to that just described for first proximal section 12. In other embodiments, second proximal section 16 can have two or more wire layers. In another embodiment, there is no second proximal section and first proximal section 12 is coupled directly to distal section 16.

In one embodiment, distal section 16 of microcatheter 10 includes distal wire layer 44, which is a single wire strand helically wound over core 30. As illustrated, distal wire layer 44 has a tapered outer diameter (OD), such that the OD of distal wire layer 44 is larger adjacent the second proximal section 14 and then gradually decreases toward the distal tip 46 of microcatheter 10. In one embodiment, the OD of distal wire layer 44 is substantially the same as the OD of the outer wire of second proximal section 16 at second junction 22. In this way, there is no change in the OD of the outer wire layer in the transition from the second proximal section 16 to the distal section 16.

Having a proximal section, or proximal sections, of multilayer wires and a distal section with a single wire layer, the microcatheter accordingly has increased relative flexibility in the distal section and has decreased relative flexibility in proximal section, which is useful in many applications, such as within the vasculature of a human or animal.

Figure 3:
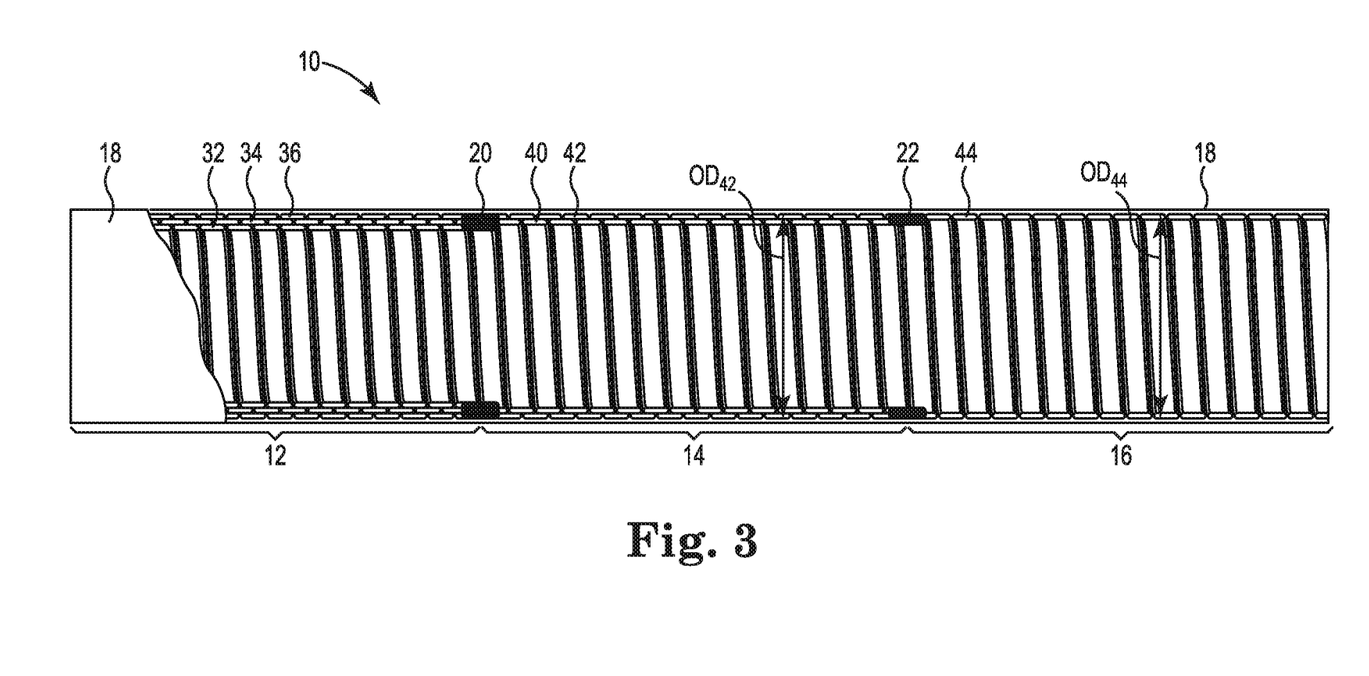
FIG. 3 illustrates an enlarged cross-sectional view of a portion of a microcatheter in accordance with one embodiment.

FIG. 3 illustrates a sectional view of a portion of microcatheter 10 in accordance with one embodiment. In FIG. 3, microcatheter 10 is sectioned down its length and the tapered portion of distal section 16 is truncated from the illustration. Also, most of polymer cover 18 is removed to reveal the inner layers. As previously described, microcatheter 10 includes first and second proximal sections 12 and 14 and distal section 16. First junction 20 couples first proximal section 12 to second proximal section 14, and second junction 22 couples second proximal section 14 to distal section 16.

In one embodiment, first proximal and second proximal sections 12 and 14 are welded together at first junction 20 and second proximal section 14 is welded to distal section 16 at second junction 22. Various laser welding or related welding can be used to form first and second junctions 20 and 22. In other embodiments, the junctions between the various sections can be accomplished with brazing, soldering, adhesives, or even a continuous wound layer, which will be further discussed below.

In one example, first proximal section 12, includes inner, intermediate and outer wire layers 32, 34, and 36, and second proximal section 14, includes inner and outer wire layers 40 and 42. In other examples, first proximal section 12 can have more or less wire layers and second proximal section 14 can have more layers in order to customize and/or optimize the pushability, trackability, and torqueability of microcatheter 10.

As illustrated in FIG. 3, distal section 16 includes distal wire layer 44, which is a single wire layer providing this section with flexibility useful for steering microcatheter 10. Furthermore, distal wire layer 44 is coupled to second proximal section 14 via second junction 22 such that the $OD_{44}$ of distal wire layer 44 substantially aligns with the $OD_{42}$ of outer wire layer 42 of second proximal section 14 at second junction 22. As such, this avoids a "step" in the outer wire layer of microcatheter 10 at second junction 22, providing a smooth OD wire profile.

Because distal wire layer 44 is a single layer of wire with a tapered OD, it is relatively flexible in order to facilitate its navigation through the tortious vascular system. Furthermore, because its tapered outer diameter is smooth without any step, it provides excellent support for smoothly transitioning through irregular-shaped paths. Because distal wire layer 44 is coupled to the OD of first or second proximal section 12 or 14, it also has excellent torque transfer between the proximal and distal sections.

In one embodiment, microcatheter 10 is configured to have a relatively thin wall and small diameter and can deliver devices used in minimally invasive applications. Microcatheter 10 is well suited to navigating the vast network of tiny arteries and veins found within the body. Because microcatheter 10 has both a relatively smaller inner diameter (ID) and outer diameter (OD) in order to reduce the overall wall thickness of the device, it is challenging to achieve the pushability, trackability, and torqueability specifications required for the different applications. Microcatheter 10 is configured to optimize pushability, trackability, and torqueability, while still having a fairly thin overall wall thickness as well as a relatively smaller OD.

In one embodiment, microcatheter 10 is configured for very small applications, such as for the vascular system of humans and animals. In some examples, the wire in wire layers 32, 34 and 36 has a wire diameter (WD) as small as 0.0005 inches up to 0.004 inches. In some examples, microcatheter 10 has an ID as small as 0.008 inches up to 0.220 inches, which also defines the diameter of the lumen within core 30 of microcatheter 10. In some examples, the OD of microcatheter 10 is 0.01 inches and 0.250 inches. Different OD and ID sizes for microcatheter 10 are also possible where various different size wire is used.

In one embodiment, inner wire layer 32 is tightly wound in a constricted state over core 30, and each subsequent wire layer, that is, intermediate wire layer 34, outer wire layer 36, etc., is tightly wound in a constricted state over the previous wire layer across the entire layer. In one embodiment, a single wire filar is used for each of inner, intermediate and outer wire layers 32, 34 and 36 without ever being cut or interrupted. In this way, inner wire layer 32 is wound on core 30, and then intermediate wire layer 34 is wound back over inner wire layer 32 without ever cutting the wire that is used to wind the layers. The same can be done for outer wire layer 36 and for any additional intermediate wire layers. Furthermore, the same can be used for inner and outer wire layers 40 and 42 of second proximal section 14, as well as for any additional wire layers used in that section.

In one embodiment, a wire for the layers in first and/or second distal sections 12 and 14 is broken or cut between each adjacent wire layer, but because each wire layer is tightly wound in a constricted state, each immediately adjacent over wire layer, that is, the wire layer subsequently wound over the previous wire layer, constrains the previous wire layer and prevents its unwinding. Because all wire layers are constrained, there is no slippage between the wire layers.

In this way, the proximal sections of microcatheter 10 that are multi-layer, such as first and second proximal sections 12 and 14, have excellent "one-to-one" torque, that is, a single full rotation at one end of the multi-layer sections of microcatheter 10 results in a single full rotation at the opposite end of a multi-layer section, rather than something less than a full rotation. Such one-to-one torque is useful in many applications, such as within the vasculature of a human or animal.

In the example illustrated in FIG. 2, inner wire layer 32 is illustrated as helically wound with a pitch in a first direction, while intermediate wire layer 34 is helically wound with a pitch in a second direction that is reverse relative to the first direction. Outer wire layer 36 is then illustrated as helically wound with a pitch substantially in the first direction, similar to inner wire layer 32. Reverse winding in this way allows microcatheter 10 to be used in rotating applications without collapsing in or winding open with the rotation of microcatheter 10. Reverse winding provides additional stability to microcatheter 10 for bi-directional rotational applications, such that it can be rotated in both clockwise and counterclockwise directions without collapsing in or winding open with the rotation. Such an embodiment may be useful in various rotational intravascular applications. Furthermore, microcatheter 10 is extremely resistant to kinking and resistant to elongation and has excellent compression resistance between adjacent filars, such that it may be useful in intravascular applications requiring pushing, pulling and bending of microcatheter 10. Despite these strengths and excellent bi-directional turning, microcatheter 10 also has excellent flexibility.

Figure 4:
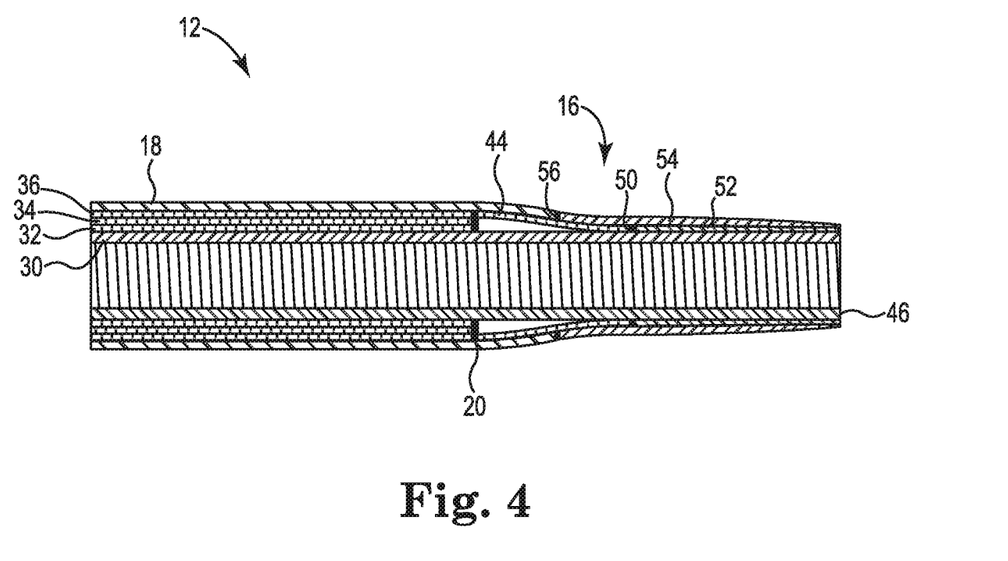
FIG. 4 illustrates an enlarged cross-sectional view of a portion of a microcatheter in accordance with one embodiment.

FIG. 4 illustrates further detail of distal section 16 of microcatheter 10 in one embodiment. In one embodiment, first proximal section 12 is coupled directly to distal section 16 via a weld at junction 20. As illustrated, distal wire layer 44 is coupled to outer wire layer 36 via a weld at junction 20 and has a tapered OD that decreases toward distal tip 46. Distal wire layer 44 terminates, however before reaching distal tip 46. At first junction 50, filler material 54 abuts distal wire layer 44 and fills in adjacent core 30 from first junction 50 out to distal tip 46. In one embodiment, filler material 52 is a polymeric material that provides further flexibility to the distal tip 46 of microcatheter 10.

In one embodiment, outer cover 18 covers first proximal section 12, junction 20 and a portion of distal wire layer 44 up to second junction 56. At second junction 56, distal jacket 54 fills in over a portion of distal wire layer 44 and over filler material 52 out to distal tip 46. In one embodiment, distal jacket 54 is a polymeric material that provides further flexibility to the distal tip 46 of microcatheter 10. Accordingly, distal section 16 has a smooth outer profile and the OD is well supported, yet flexible for good steerability.

In one embodiment, outer cover 18 has a relatively uniform thickness along the entire length of microcatheter 10. In one embodiment, distal jacket 54 has a thickness that substantially matches that of outer cover 18 at second junction 56, but then gets thinner out toward distal tip 46. In this way, the OD of microcatheter 10 gets smaller out toward distal tip 46. Also, in one embodiment, different polymer materials are used for outer cover 18 and distal jacket 54, such that flexibility of distal section 16 can accordingly be adjusted and customized to each particular application. Similarly, the material of filler layer 52 can be adjusted to be customized to each particular application as well.

In one embodiment, because first and second junctions 50 and 56 are offset along the length of microcatheter 10, distal jacket 54 overlaps a portion of distal wire layer 44, thereby providing a good means of securing distal jacket 54 on microcatheter 10. At the same time, this configuration allows for distal wire layer 44 to terminate before distal tip 46, so the filler layer 52 can provide increased flexibility at distal tip 46.

Figure 5:
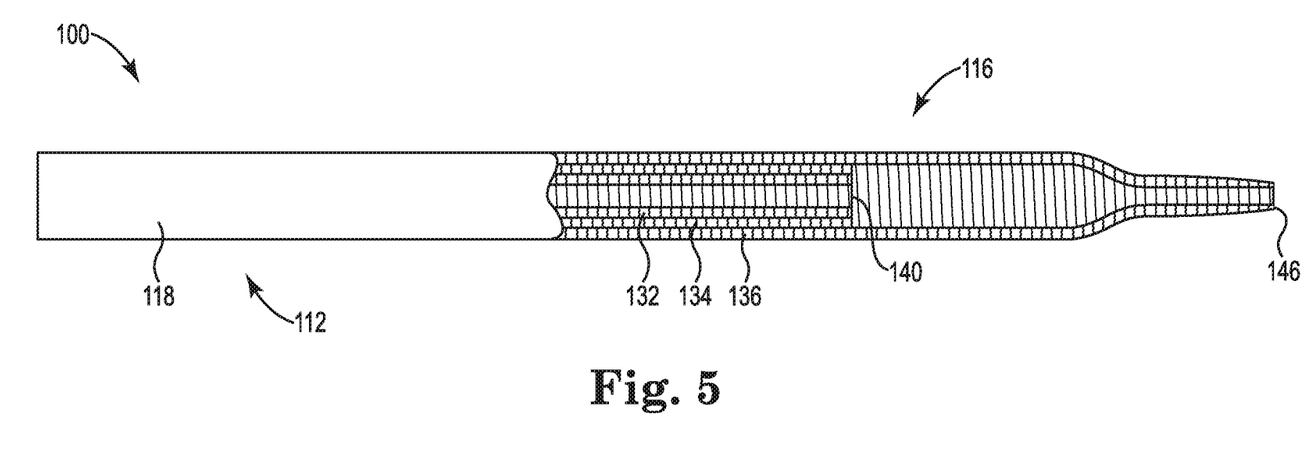
FIG. 5 illustrates an enlarged cross-sectional view of a portion of a microcatheter in accordance with one embodiment.

FIG. 5 illustrates a partial sectional view of a portion of microcatheter 100 in accordance with one embodiment. Similar to previously described, microcatheter 10, microcatheter 100 includes at least one proximal section 112 (and optionally additional proximal sections) and distal section 116. All sections of microcatheter 100 are covered with a polymer cover 118. In the figure, most of polymer cover 118 is removed to reveal the inner layers.

In one example, proximal section 112, includes inner, intermediate and outer wire layers 132, 134, and 136. Similar to that described above, each of the wire layers is tightly wound in a constricted state over a wire layer below it, or over a core (not illustrated in FIG. 5). In other examples, proximal section 112 can have more or less wire layers, and additional proximal sections can be added, in order to customize and/or optimize the pushability, trackability, and torqueability of microcatheter 100. In some embodiments, additional intermediate layers provide additional stiffness and add further strength to the microcatheter to prevent kinking and provide resistance to elongation, and has excellent compression resistance between adjacent filars.

In one embodiment, proximal section 112 is coupled to distal section 116 by the continuous winding of outer wire layer 136. While inner and intermediate wire layers 132 and 134 terminate at junction 140 between proximal section 112 and distal section 116, outer wire layer 136 is continuously wound from the proximal section 112 into the distal section 116 and continuing out to the distal tip 146. In one embodiment, the OD of outer wire layer 136 gradually decreases in the distal section 116 toward the distal tip 146 of microcatheter 100. Because the continuous winding of outer wire layer 136 essentially couples proximal section 112 and distal section 116, microcatheter 100 does not need a weld at junction 140 to join proximal and distal sections 112 and 116.

As illustrated in FIG. 5, similar to that described above, distal section 116 includes a single wire layer, outer wire layer 136, which provides this section with flexibility useful for steering microcatheter 100. Furthermore, because outer wire layer 136 in distal section 116 is the same as in proximal section 114, the OD of microcatheter 100 does not shift at all between the proximal and distal sections 112 and 116 and is completely supported by outer wire layer 136. Similar to microcatheter 10 above, microcatheter 100 also avoids a "step" in its outer layer providing a smooth OD profile and excellent support for smoothly transitioning through irregular-shaped paths. Because outer wire layer 136 is continuously wound from proximal section 112 out to distal tip 146, microcatheter 100 also has excellent torque transfer between those sections.

Figure 6:
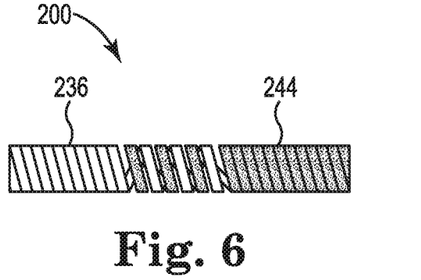
FIG. 6 illustrates an enlarged cross-sectional view of a connected portion of a microcatheter in accordance with one embodiment.

FIG. 6 illustrates a partial view of a portion of microcatheter 200 in accordance with one embodiment. In one embodiment, first wire layer 236 is coupled with second wire layer 244. FIG. 6 illustrates an embodiment for coupling two portions of a microcatheter, such as joining first and second proximal sections 12 and 14 of microcatheter 10, first proximal section 12 with distal section 16 of microcatheter 10, or the like.

In one embodiment, an end portion of each of first wire layer 236 and second wire layer 244 is open wound, such that the two open wound end portions can be screwed together. Each end portion is open wound in an opposite winding direction so that the end portions of first wire layer 236 and second wire layer 244 can be interlocked. In one embodiment, the connection between first wire layer 236 and second wire layer 244 is further secured by adhesive or glue. In another embodiment, the connection between first wire layer 236 and second wire layer 244 is further secured by use of solder or welding.

The illustrations herein primarily show the wire that is used in the various wire layers as flat or rectangular, but other shapes can be used in accordance with other embodiments. For example, round wire or other shapes can be used. In some embodiments, the wire in the various wire layers can be made from one or more of stainless steel, Nitinol®, MP35N, titanium and tantalum. Also, in various embodiments, outer covers for the microcatheters can be made from one or more of pebax, nylon, PET, FEP, and polyurethane. The core within the various wire layers can be made from one or more of polyimide, PTFE, pebax, nylon, polyurethane, HDPE, and PEEK.

The illustrated wire layers can be wound in variety of ways according to embodiments. In one embodiment, one convolution of wire is wound at one time for each of the wire layers. In another embodiment, microcatheter 10 is a multifilar construction, where multiple convolutions of adjacent wire are wound at once. Two, three, four, five or more adjacent wire helices can be wound within each layer at one time. Furthermore, each of the wire layers may be wound with a single wire filar, or each layer can be wound with strands of wire so that each layer has adjacent strands of wire.

The combination of the multilayer wire proximal section or sections with single layer wire distal sections, and smooth transition between these sections without a step in the outer profile, for microcatheters 10, 100 and 200 described above provide excellent steerability and are optimize to provide superior pushability, trackability, and torqueability, while still having a fairly thin overall wall thickness as well as a relatively smaller OD. Inner lumen, within core 30 for example, provides access for guidewires during initial insertion, as well as providing generous access for tools and delivery once the microcatheter is placed. In addition, by joining one or more multilayer wire proximal sections, such as first and second proximal sections 12 and 14 discussed above, microcatheters in accordance with the embodiments herein allow for overall longer lengths extending radial access for additional applications, while still maintaining excellent steerability, pushability, trackability, and torqueability.

Figure 7:
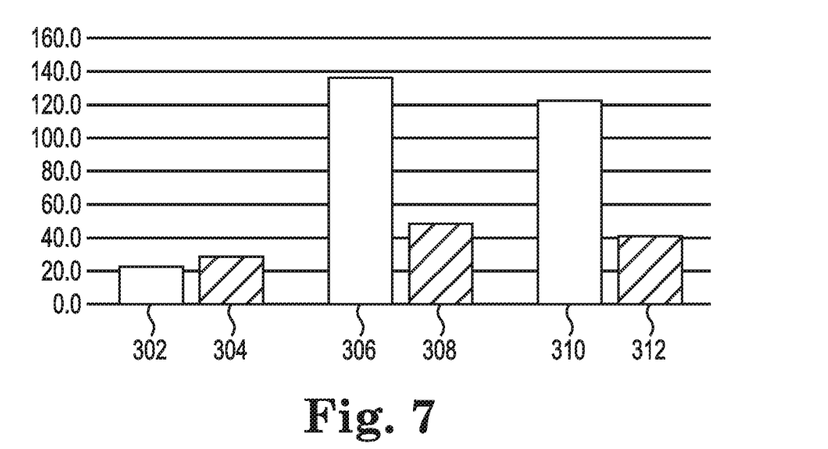
FIG. 7 illustrates a graph of a comparison of the trackability of various microcatheter configurations.

When compared with prior art microcatheters, which for example use braids or the like rather than multi-layer windings, microcatheters 10, 100 and 200 described above provide superior performance results. For comparison, three microcatheters were inserted into a tortuous path, and measurements were taken for each on how much force it takes to 1) push the microcatheter forward into the tortuous path and 2) pull the microcatheter backward through the tortuous path. This is often referred to as the trackability. FIG. 7 is a graph reflective of a comparison of the trackability of various microcatheter configurations.

In FIG. 7, for a microcatheter in accordance with the present embodiments 10, 100 and 200 described herein (A), the insertion force was 22.50 grams, illustrated in column 302, and the withdrawal force is illustrated was 28.80 grams, illustrated in column 304. For a first microcatheter in accordance with the prior art (B), the insertion force was 137.22 grams, illustrated in column 306, and the withdrawal force was 48.83 grams, illustrated in column 308. For a second microcatheter in accordance with the prior art (C), the insertion force was 123.14 grams, illustrated in column 310, and the withdrawal force was 41.61 grams, illustrated in column 312. As is apparent, a microcatheter A in accordance with the present embodiments has much lower insertion and withdrawal forces than prior art microcatheters B and C.

Figure 8:
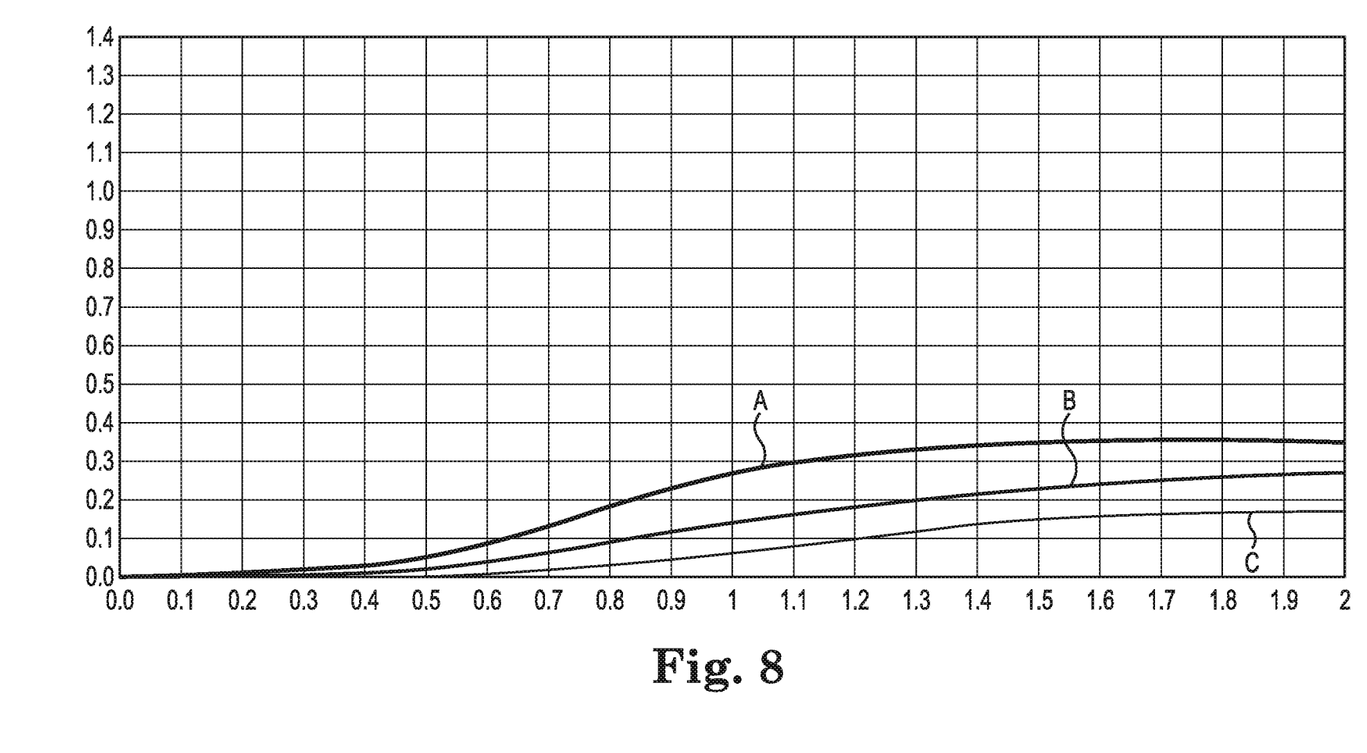
FIG. 8 illustrates a graph of a comparison of the pushability of various microcatheter configurations.

In addition, comparative measures of pushability for the same three microcatheters are illustrated in FIG. 8. Pushability is a measure of how much force the microcatheter can push to get across a tight lesion or other obstruction in the vasculature. For comparison, the three microcatheters were inserted into a tortuous path over a guide wire. A load cell was then used to measure how much force the tip of each microcatheter is able to push forward. The proximal end of each microcatheter was pushed forward different distances from a starting point of zero and measure how much force the microcatheter is pushing on the load cell at the tip. Higher forces show a better transmission of force from the input side to the tip. The table below illustrates the force of each of the three microcatheters corresponding the distance pushed.

TABLE 1

| Distance (cm) | A (force lbf) | B (force lbf) | C (force lbf) |
|---|---|---|---|
| 0 | 0 | 0 | 0 |
| 0.5 | 0.05 | 0.02 | 0 |
| 1 | 0.27 | 0.14 | 0.06 |
| 1.5 | 0.35 | 0.23 | 0.15 |
| 2 | 0.35 | 0.27 | 0.17 |

FIG. 8 plots these measurements for each of microcatheters A, B and C. As is apparent, a microcatheter A in accordance with the present embodiments has higher pushability than prior art microcatheters B and C, and better transfers force from the input to the tip.

Although specific embodiments have been illustrated and described herein, it will be appreciated by those of ordinary skill in the art that a variety of alternate and/or equivalent implementations may be substituted for the specific embodiments shown and described without departing from the scope of the embodiments. This application is intended to cover any adaptations or variations of the specific embodiments discussed herein. Therefore, it is intended that these embodiments be limited only by the claims and the equivalents thereof.

What is claimed is:

1. A microcatheter comprising:
an inner polymeric tube defining an inner lumen;
a proximal section comprising an inner wire layer helically wound in a constricted state over the inner polymeric tube and further comprising an outer wire layer helically wound over the inner wire layer in a constricted state within the proximal section, the outer wire layer having an outer diameter; and
a distal section comprising a distal wire layer helically wound in a constricted state and having an outer diameter;
wherein the proximal and distal sections are joined at a junction, and wherein the inner wire layer, the outer wire layer and the distal wire layer are all immediately adjacent the junction and the inner wire layer extending throughout the proximal section and not extending into the distal section; and
characterized in that the outer diameter of the outer wire layer of the proximal section is substantially the same as the outer diameter of the distal wire layer of the distal section at the junction between the proximal and distal sections and characterized by the absence of a step between the outer diameter of the outer wire layer and the outer diameter of the distal wire layer at the junction.

2. The microcatheter of claim 1 further comprising an outer polymer cover surrounding the inner and outer wire layers and at least a portion of the distal wire layer, thereby securing the wire layers within the outer polymer cover.

3. The microcatheter of claim 1, wherein no portion of the inner wire layer extends into the distal section and wherein the distal section has only a single wire layer comprising the distal wire layer.

4. A microcatheter having proximal and distal sections that are joined at a junction, the microcatheter comprising:
an inner polymeric tube defining an inner lumen;
an inner wire layer helically wound in a constricted state over the inner polymeric tube, the inner wire layer extending throughout the proximal section and not extending into the distal section;

an outer wire layer helically wound over the inner wire layer in a constricted state within the proximal section, the outer wire layer having an outer diameter; and a distal wire layer helically wound in a constricted state within the distal section and having an outer dimeter that is substantially the same as the outer diameter of the outer wire layer at the junction where the proximal and distal sections are joined, and wherein the inner wire layer, the outer wire layer and the distal wire layer are all immediately adjacent the junction; and an outer polymer cover surrounding the inner and outer wire layers thereby securing the wire layers within the outer polymer cover;

characterized by the absence of a step between the outer diameter of the outer wire layer and the outer diameter of the distal wire layer at the junction.

5. The microcatheter of claim 4, wherein the outer wire layer of the proximal section and the distal wire layer of the distal section is a continuously wound single wire without a break between the proximal and distal sections.

6. The microcatheter of claim 4, wherein the outer wire layer of the proximal section is welded to the distal wire layer of the distal section.

7. The microcatheter of claim 4, wherein the outer polymer cover surrounds the inner and outer wire layers of the proximal section and at least a portion of the distal wire layer of the distal section thereby securing the wire layers within the outer polymer cover.

8. The microcatheter of claim 4 further comprising an intermediate wire layer helically wound over the inner wire layer in a constricted state, the outer wire layer being helically wound over the intermediate wire layer.

9. The microcatheter of claim 4, wherein the microcatheter has a distal tip, and further comprising a filler layer between the distal wire layer and the distal tip.

10. The microcatheter of claim 9, wherein the distal wire layer has a tapered outer diameter with a larger outer diameter where the proximal and distal sections are joined and a smaller outer diameter at the distal tip.

11. The microcatheter of claim 9 further comprising a distal jacket completely covering the filler layer and at least partially covering the distal wire layer.

12. The microcatheter of claim 11, wherein the filler layer has a thickness substantially the same as the thickness of the distal wire layer such that the distal jacket has a smooth profile at a junction of the filler layer and the distal wire layer.

13. The microcatheter of claim 4, wherein the inner lumen has a diameter that is between 0.008 inches and 0.220 inches, an outer diameter of the microcatheter is between 0.01 inches and 0.250 inches, and a diameter of the wire in each of the inner wire layer, outer wire layer and distal wire layer is between 0.0005 inches and 0.004 inches.

14. A method of forming a microcatheter comprising:

forming an inner polymeric tube defining an inner lumen;

helically winding an inner wire layer in a constricted state over the polymeric tube;

helically winding an outer wire layer over the inner wire layer in a constricted state, wherein the outer wire layer has an outer diameter and the inner and outer wire layers comprise a proximal section; and helically winding a distal wire layer in a constricted state, wherein the distal wire layer has an outer diameter, the distal wire layer comprises a distal section, and the proximal and distal sections are joined at a junction, and wherein the inner wire layer, the outer wire layer and the distal wire layer are all immediately adjacent the junction;

wherein no portion of the inner wire layer extends into the distal section and wherein the distal section has only a single wire layer comprising the distal wire layer;

wherein the outer wire layer and the distal wire layer are wound such that the outer diameter of the outer wire layer is substantially the same as the outer diameter of distal wire layer at the junction where the proximal and distal sections are joined and characterized by the absence of a step between the outer diameter of the outer wire layer and the outer diameter of the distal wire layer at the junction.

15. The method of claim 14 further comprising forming an outer polymer cover surrounding the proximal section and at least a portion of the distal section, thereby securing the wire layers within the outer polymer cover.

16. The method of claim 14, wherein the outer wire layer of the proximal section and the distal wire layer of the distal section are wound as a continuously wound single wire without a break between the proximal and distal sections.

17. The method of claim 14 further comprising welding the outer wire layer of the proximal section to the distal wire layer of the distal section.

* * * * *